United States Patent [19]

Spotorno et al.

[11] Patent Number: 5,549,695
[45] Date of Patent: Aug. 27, 1996

[54] COMPOSITE ARTIFICIAL SOCKET AND HIP JOINT PROSTHESIS

[75] Inventors: Lorenzo Spotorno, Finale Ligure, Italy; Roland Willi, Neftenbach, Switzerland

[73] Assignee: Sulzer Medizinaltechnic AG, Winterthur, Switzerland

[21] Appl. No.: 291,384

[22] Filed: Aug. 16, 1994

[30] Foreign Application Priority Data

Aug. 30, 1993 [EP] European Pat. Off. ............... 93810618

[51] Int. Cl.⁶ .................. A61F 2/34; A61F 2/30
[52] U.S. Cl. ........................... 623/22; 623/18
[58] Field of Search ................... 623/16, 18, 21, 623/19, 22, 23

[56] References Cited

FOREIGN PATENT DOCUMENTS

| | | |
|---|---|---|
| 0169978 | 2/1986 | European Pat. Off. . |
| 0341199 | 11/1989 | European Pat. Off. . |
| 0420795 | 4/1991 | European Pat. Off. . |
| 0445068 | 9/1991 | European Pat. Off. . |
| 0482320 | 4/1992 | European Pat. Off. . |
| 2597329 | 10/1987 | France . |
| 2645433 | 10/1990 | France . |
| 3341723C1 | 3/1985 | Germany . |
| 3602081 | 10/1986 | Germany . |
| WO85/00284 | 1/1985 | WIPO . |

Primary Examiner—David Isabella
Attorney, Agent, or Firm—Townsend and Townsend and Crew

[57] ABSTRACT

The socket (2) comprises a metallic outer shell (4), an intermediate shell (5) of plastics and a metallic inner shell (6), which may be inserted into the latter using a connection by shape. The outer shell (4) is divided into segments (4a, 4b, 4c, 4d, 4e) by recesses (9) open towards its equatorial marginal region. The outer shell (4) and the inner shell (6) are rigidly supported against each other in the direction of a common main axis (A) by a contact portion (8), and are non-rotatably connected by an attachment element (15) eccentrically offset with respect to the main axis (A). The intermediate shell (5) has an aperture (20), which receives the contact portion (8), and an outer surface (21), which has a supporting portion (21a) for bearing onto a portion of the inner surface (18) of the outer shell (4), and outside this supporting portion (21a) delimits with the remaining portion of the inner surface (18) a spacing (S), which allows corresponding relative movement of the intermediate shell (5), which contains the inner shell (6), and at least one of the segments (4a, 4b, 4c, 4d, 4e) of the outer shell (4) transversely to the main axis (A). The implanted outer shell (4) may, under load, elastically deform with the part of the bone by which it is surrounded, while the spherical shape of the inner shell (6) remains undisturbed.

10 Claims, 3 Drawing Sheets 5,549,695

COMPOSITE ARTIFICIAL SOCKET AND HIP JOINT PROSTHESIS

FIELD OF THE INVENTION

The invention relates to a joint socket and also to a hip joint prosthesis with such a socket.

BACKGROUND OF THE INVENTION

Conventional hip joint sockets typically in include an outer shell with a closed, relatively rigid equatorial marginal portion and with segments which move around it and which are equipped with free end portions, directed against the pole region of the outer shell and deflectable inwardly against the pole region, the free end portions are provided with tips which may be pressed into the osseous tissue (FR-A-2 645 433). In this known embodiment, the end parts of the segments, facing the pole region, are, during insertion of the outer shell into the implantation zone, pushed inwardly and subsequently by an intermediate shell. The shell may be mounted for connection by shape in the outer shell, pushed outwardly and attached by the tips, pushed into the osseous tissue, in the section of the implantation zone adjacent the pole region of the outer shell. The outer shell, the intermediate shell and the inner shell insertable therein may be assembled to form an implant which has, as a whole, a stable shape and which provides a relatively rigid connection between the inner shell, which receives a joint head, and the osseous tissue. It has been found that, when such relatively rigid sockets are used under load, parts of the osseous tissue may be locally detached from the outer shell, for instance, due to elastic deformation of the bone portion surrounding the outer shell, for instance during widening of a part of the implantation zone. Thus, corresponding, relatively high local loading of the osseous tissue may arise in the remaining part of the implantation zone.

SUMMARY OF THE INVENTION

The aim of the invention is to devise an improved socket, and which ensures between the inner shell and the osseous tissue a connection yieldable within pre-determined limits and by which may be achieved substantially non-variable loading of the osseous tissue even during elastic deformation of the bone portion receiving the socket.

The design of the socket, according to the invention, enables adaptation of the equatorial marginal portion of the outer shell, which portion is divided into segments, to the deformation of the surrounding bone portion, which deformation is caused during loading. Thus, even in the case of loading by varying forces, a connection by friction and shape is ensured between all the segments of the outer shell, which are movable relative to each other, and the osseous tissue. Correspondingly local detachment of the osseous tissue from a part or parts of the outer shell may be avoided, thereby preventing disadvantageous irregular loading of the osseous tissue by locally arising increased compressional forces. Due to the spacing between the outer shell and the intermediate shell, the intermediate shell and the inner shell may, under the influence of varying forces, move correspondingly to and fro about the attachment element while the spherical shape of the inner shell remains available for the guiding of the joint head.

BRIEF DESCRIPTION OF THE DRAWINGS

Further details and features are apparent from the following description of embodiments of the invention, shown diagrammatically in the drawing, in connection with the claims. In the drawing

DESCRIPTION OF THE PREFERRED EMBODIMENT

Figure 1:
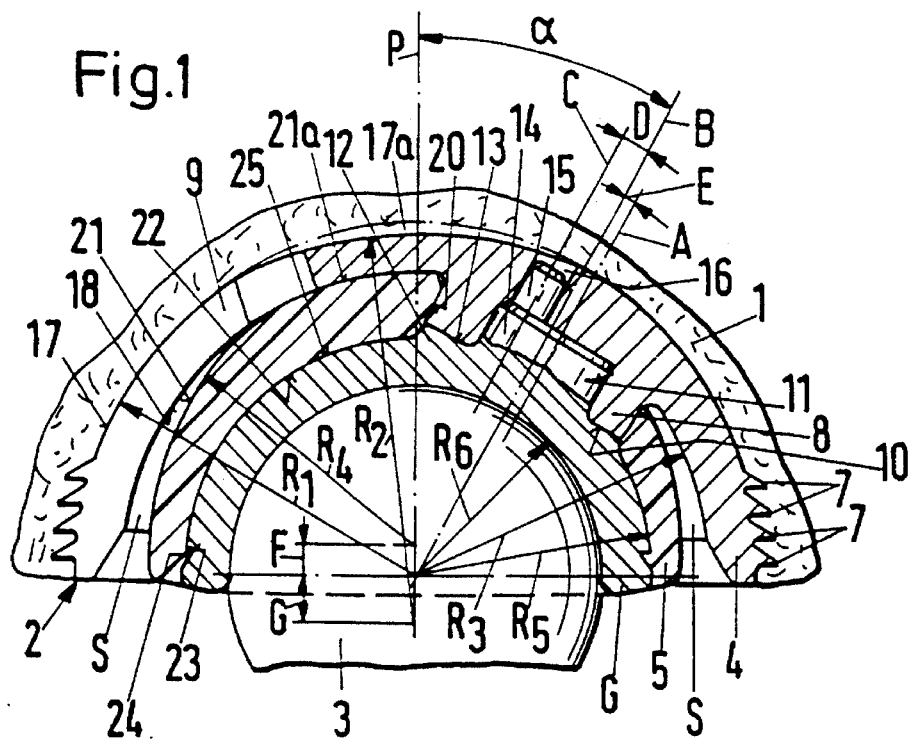
FIG. 1 shows a part of a hip joint prosthesis with a socket according to the invention in a diametrically extending section.
Figure 2:
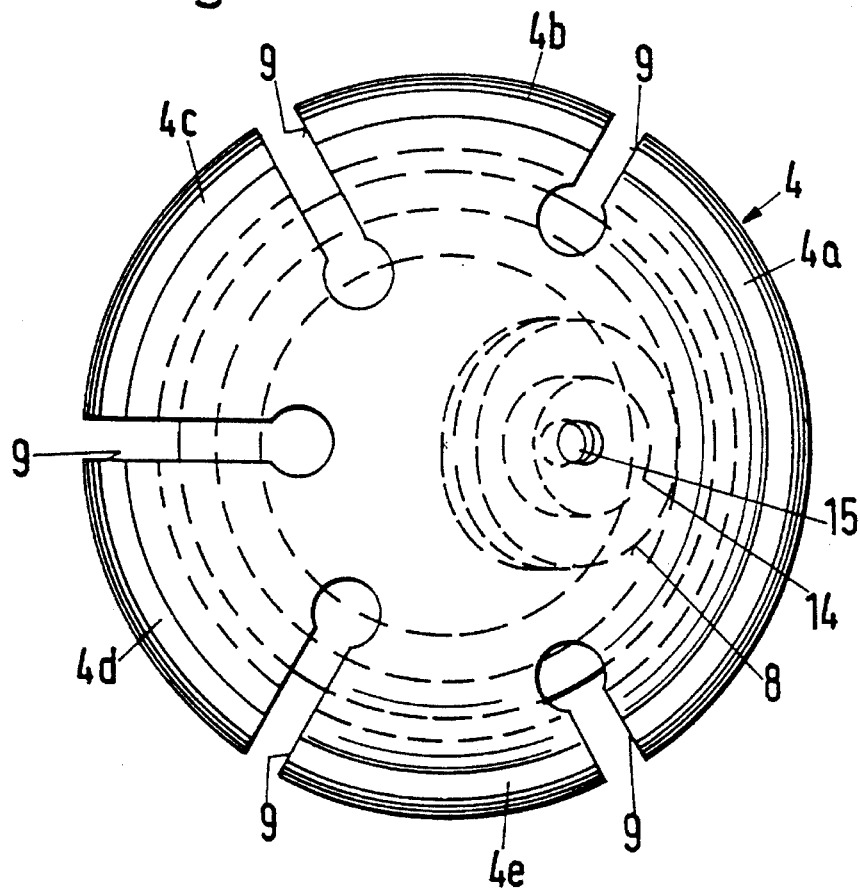
FIG. 2 is a plan view of the socket according to FIG. 1.

The hip joint prosthesis according to FIGS. 1 and 2 comprises a composite socket 2, which may be inserted into the osseous tissue 1 of a human pelvis portion, and a joint head 3, which is situated on a shaft portion (not shown) attachable in a manner known per se in a tubular bone, in the present example in a femur. The socket 2 comprises a metallic outer shell 4, which may be inserted into a prepared recess in the osseous tissue 1 and fixed therein, the outer shell 4 having substantially the shape of a hollow hemisphere. The socket 2 further comprises an intermediate shell 5, which may be inserted into the outer shell, is of plastics and is also substantially hemispherical, and a hemispherical inner shell 6, which may be inserted into the intermediate shell and retained therein by shape and situated substantially concentrically to the outer shell 4. The inner shell 6 receives a joint head 3.

The outer shell 4 is divided by recesses 9, which extend from its equatorial peripheral region along meridians towards its pole region, into several (in the illustrated example five) segments 4a, 4b, 4c, 4d, 4e movable relative to each other, which may be correspondingly, under self-contained stress, inserted into the implantation zone and be deformable with respect to the osseous tissue. The outer shell 4 is further provided in the equatorial peripheral region with several tooth-like projections 7, which extend in the peripheral direction and may be introduced, pressed or driven home into the osseous tissue, and by means of which the segments 4a, 4b, 4c, 4d, 4e may be attached in the osseous tissue 1 surrounding the implantation zone. The outer shell 4 and the inner shell 6 are connected to each other in the direction of a common main axis A, which is at least approximately radial, the connection being rigid and non-rotatable with respect to this main axis A. For this reason, the outer shell 4 is equipped with a contact portion 8, which faces inwardly, has a contact surface 10 facing the inner shell 6, and an inwardly open guiding bore 11, while the inner shell 6 is provided with a supporting portion 12, which has a supporting surface 13 which may bear against the contact surface 10, and a pin-shaped guiding portion 14, which extends outwardly therefrom and may be inserted into the guiding bore 11. In order to safeguard the non-rotatable connection between the outer shell 4 and the inner shell 6, an attachment element may be provided on the guiding portion 14. In the illustrated example, the attachment element has the shape of a centring pin 15, has an axis C eccentrically offset by a value D with respect to the main axis A, and may be inserted into a corresponding recess 16 provided in the outer shell 4.

The common main axis A of the outer shell 4 and the inner shell 6 may substantially coincide with the line of action of a main loading force B transmitted through the socket 2. The line of action is determined by anatomical conditions in the pelvis region, or, as shown in FIG. 1, it may be displaced with respect to this line of action by a value E, determined e.g. structurally, the line of action making an angle a with a pole axis P of the outer shell 4. In the illustrated example, the outer shell 4 has a smaller wall in a pole region 17a than in the equatorial region and has an outer surface 17 with a spherical main portion, determined by a radius R1, and a flattened portion in the pole region 17a, the flattened portion being determined by a larger radius R2, and also a spherical inner surface 18 determined by a radius R3. The smaller wall thickness of the outer shell 4 in the pole region 17a allows elastic deformation of the segments 4a, 4b, 4c, 4d, 4e in a predetermined bending region and simplifies the insertion of the outer shell 4 and its primary attachment in the implantation zone.

The intermediate shell 5 has an aperture 20, which is suitable for the admission of the contact portion 8 and the supporting portion 12 and has also a spherical outer surface 21 and a spherical inner surface 22 whose centres of curvature may be, in the illustrated example, eccentrically offset with respect to each other on the pole axis P by a value F. The outer surface 21 and the inner surface 22 are determined by radii R4 and R5, the radius R4 being by a value corresponding to a predetermined spacing S smaller than the radius R3 of the inner surface 18 of the outer shell 4. As is apparent from FIG. 1, the intermediate shell 5 has a supporting portion 21a which may bear onto the inner surface 18 of the outer shell 4 only at its pole region, and extends outside this region at a distance from the inner surface 18. This distance increases towards the equatorial region of the outer shell 4. The spacing S enables corresponding relative movement of the equatorial regions of the intermediate shell 5, which is firmly connected to the inner shell 6, and of at least one of the segments 4a, 4b, 4c, 4d, 4e transversely to the main axis A. According to the illustration in FIG. 1, the inner shell 6 may be provided in the equatorial region of its outer surface 25 with an annular groove 23 which serves for the admission of a rim 24. The rim 24 projects from the inner surface 21 of the intermediate shell 5 inwardly and may engage into the annular groove 23.

The described arrangement enables, simply and quickly, accurate positioning of the socket 2 in the correspondingly prepared implantation zone, while the outer shell 4, the intermediate shell 5 and the inner shell 6 may be inserted either one after another or after having been first assembled to an implantation unit. The described connection by friction and shape between the contact portion 8 of the outer shell 4 and the supporting portion 12 of the inner shell 6 ensures, in a simple manner, a reliable direct transmission of the main loading force B and also a reliable, angularly correct guiding of the joint head 3. At the same time, the inner shell 6 is held substantially in a basic position concentric with the inner surface 18 of the outer shell 4. The segments 4a, 4b, 4c, 4d, 4e of the outer shell 4, which are deformable about the pole region 17a and the contact portion 8, and are movable relative to each other in the manner of bendable springs, enable corresponding deformation, due to loading, of the implantation zone, e.g. local constrictions in one section and corresponding widenings in another section of the recess in the osseous tissue 1, surrounding the outer shell 4. These deformations are limited by the dimensions of the intermediate shell 5 and they prevent local detachment of the segments from the osseous tissue 1 on the appearance of the widenings.

Figure 3:
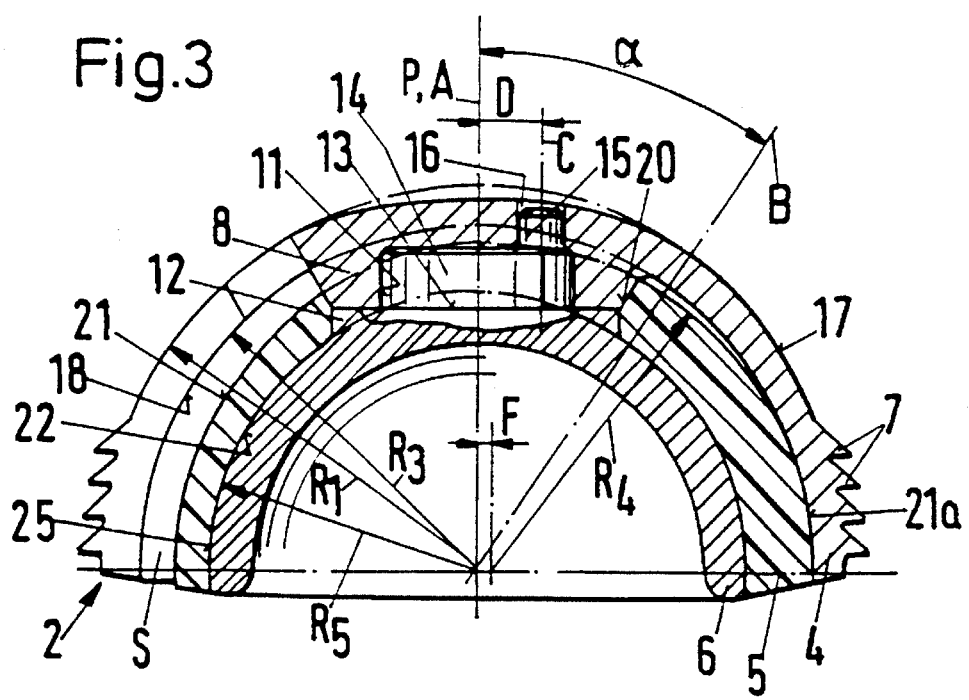
FIG. 3 shows a socket in a diametrically extending section according to a modified embodiment.
Figure 4:
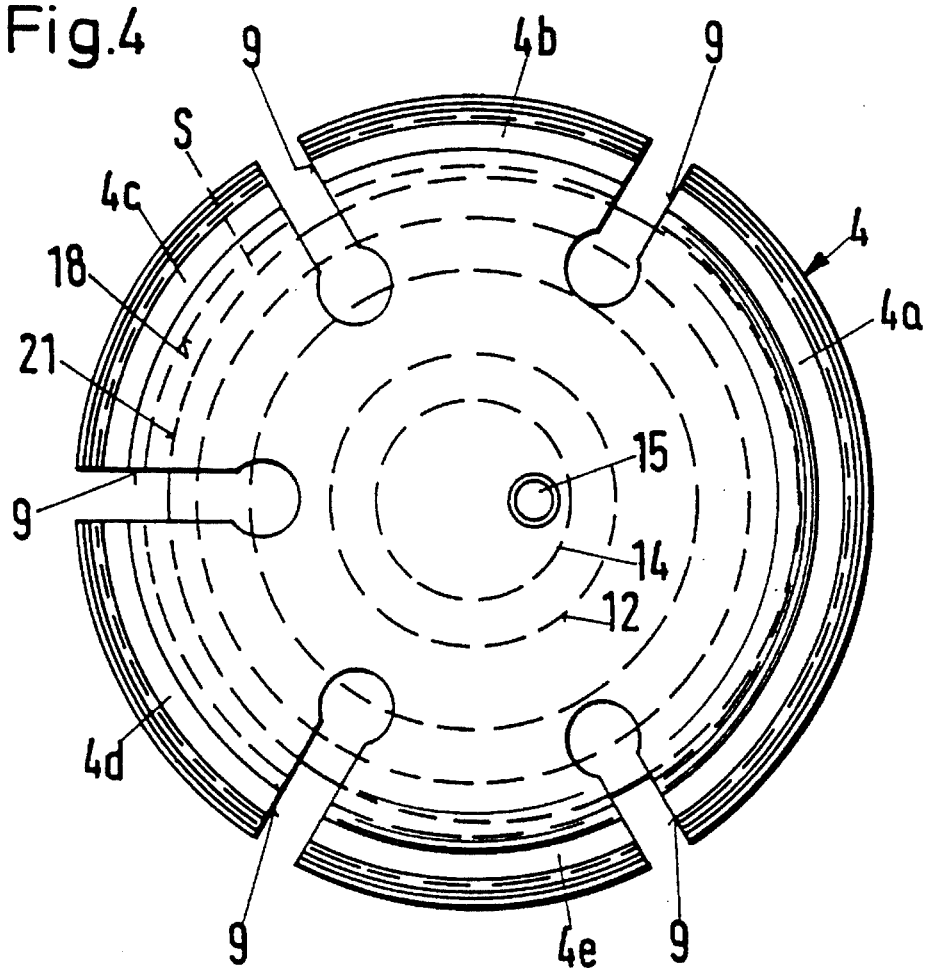
FIG. 4 is a plan view of the socket according to FIG. 3.

In the illustrated embodiments, corresponding parts have the same references. According to the illustration in FIGS. 3 and 4, the common main axis A, which is decisive for the connection by friction and shape between the outer shell 4 and the inner shell 6, may coincide with the pole axis P, which is offset with respect to the line of action of the main loading force B. Correspondingly both the contact portion 8 of the outer shell 4 and the supporting portion 12 of the inner shell 6 is formed in the corresponding pole region. In this embodiment the centres of curvature of the outer surface 21 and the inner surface 22 of the intermediate shell 5 are offset laterally with respect to each other in the region of a common equatorial plane. The supporting surface 21a of the intermediate shell 5 bears correspondingly onto the inner surface 18 of the outer shell 4 only in the equatorial marginal region, so that the intermediate shell 5 and the outer shell 4 delimit a spacing S, which is sickle-shaped in plan view (FIG. 4). This spacing enabling corresponding relative movement of the intermediate shell 5 and the segments 4b, 4c, 4d, 4e of the outer shell 4, while a relatively rigid connection exists between the segment 4a and the intermediate shell 5, which ensures reliable transmission of the main loading force B between the inner shell 6 and the outer shell 4.

Figure 5:
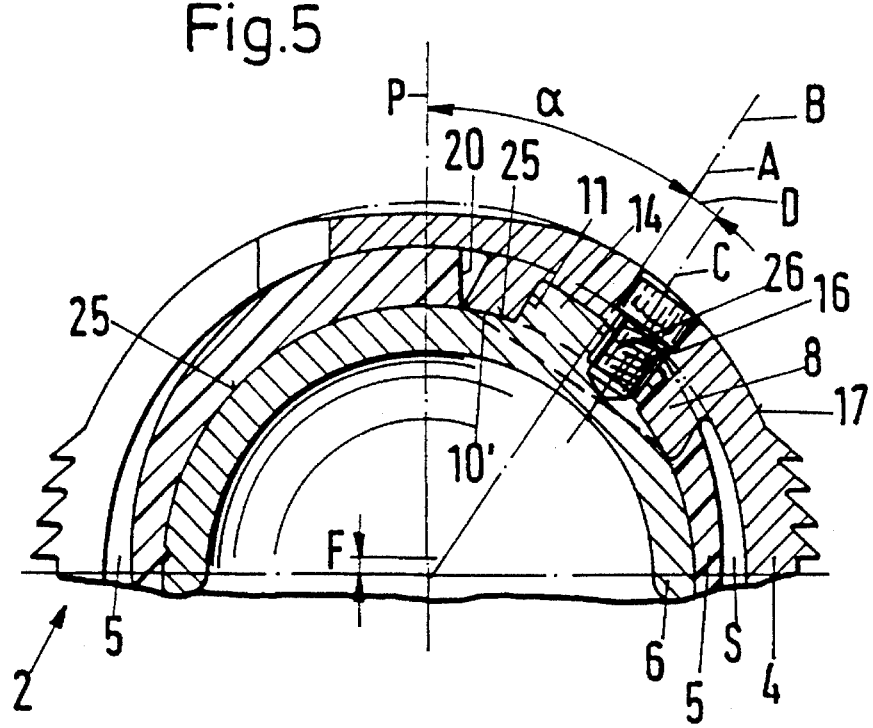
FIG. 5 shows a socket in a diametrically extending section according to a further embodiment.
Figure 6:
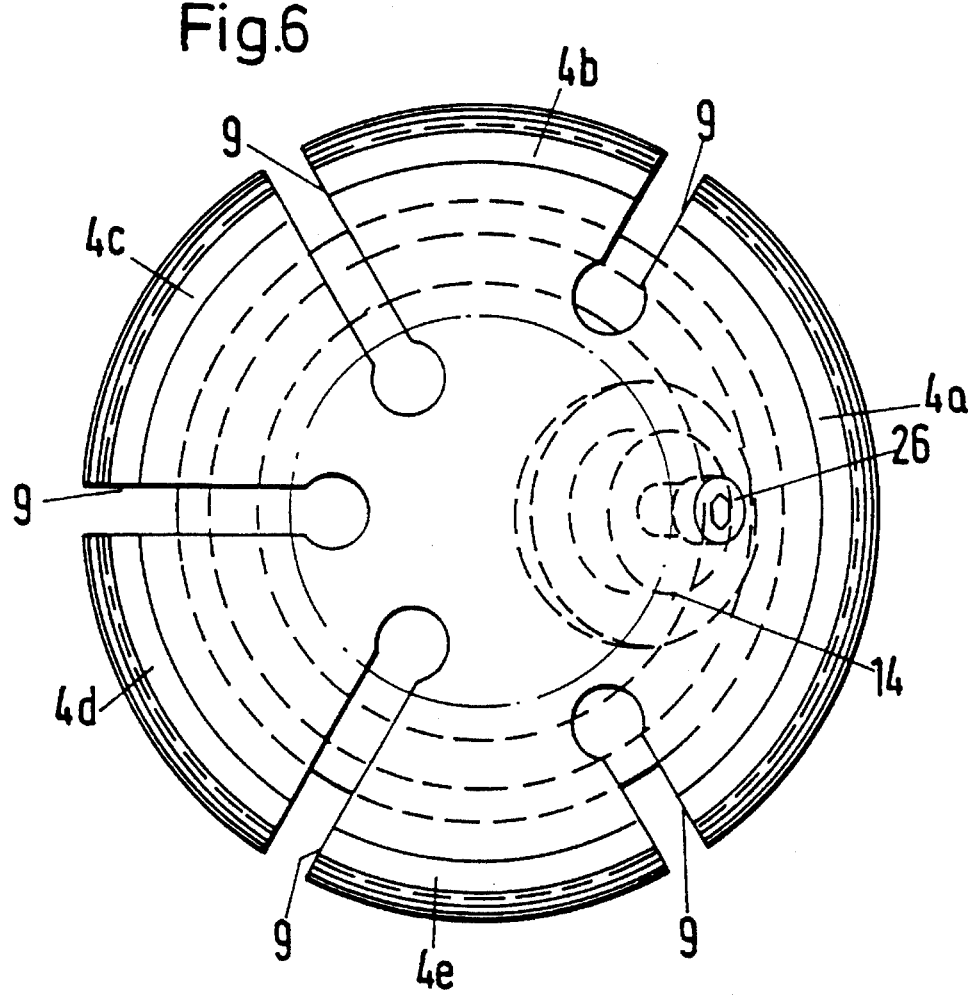
FIG. 6 is a plan view of the socket according to FIG. 5.

The socket 2 according to FIGS. 5 and 6 corresponds substantially to the embodiment according to FIGS. 1 and 2. In contrast to this embodiment, the contact portion 8 is formed with a spherical contact surface 10' which may bear on a part 25' of the spherical outer surface 25 of the inner shell 6. As a consequence, it is not necessary to make a supporting portion on the inner shell 6 which would fit the contact portion 8 and would have to be additionally machined. Thus, in comparison with the earlier described embodiments, the inner shell may be of a simple design which requires only the formation of a simple cylindrical extension as a guiding portion 14. A screw 26 may be used a fixing element for ensuring non-rotatable connection between the outer shell 4 and the inner shell 6, and it may be inserted into the guiding portion 14 from outside and is eccentrically offset with respect to the main axis A. The screw 26 connects the outer shell 4, the intermediate shell 5 and the inner shell 6 to an earlier assembled unit which may be implanted as a whole. As is apparent from FIG. 5, the main axis A may coincide with the line of action of the main loading force B.

The embodiment according to FIGS. 5 and 6 provides a socket 2 of a structurally simple and advantageously compact design.

The invention could be described in a condensed manner as follows:

The socket 2 comprises a metallic outer shell 4, an intermediate shell 5 of plastics and a metallic inner shell 6 which may be inserted into the latter using a connection by shape. The outer shell 4 is divided into segments 4a, 4b, 4c, 4d, 4e by recesses 9 open towards its equatorial marginal region. The outer shell 4 and the inner shell 6 are rigidly supported against each other in the direction of a common main axis A by a contact portion 8, and are non-rotatably connected by an attachment element 15 eccentrically offset with respect to this main axis A. The intermediate shell 5 has an aperture 20, which receives the contact portion 8, and an outer surface 21 which has a supporting portion 21a for bearing onto a portion of the inner surface 18 of the outer shell 4, and, outside this supporting portion 21a, delimits with the remaining portion of the inner surface 18 a spacing S, which allows corresponding relative movement of the intermediate shell 5, which contains the inner shell 6, and at least one of the segments 4a, 4b, 4c, 4d, 4e of the outer shell 4 transversely to the main axis A. The implanted outer shell 4 may, under load, elastically deform with the part of the bone by which it is surrounded, while the spherical shape of the inner shell 6 remains undisturbed.

We claim:

1. A composite artificial socket comprising:

an outer shell having a substantially hemispherical inner surface with a main axis extending in a substantially radial direction, the outer shell being adapted for insertion into an implantation zone, the outer shell having recesses extending along meridians in the outer shell, the recesses defining movable segments adapted for attachment to osseous tissue within the implantation zone;

an intermediate shell having substantially hemispherical inner and outer surfaces;

an inner shell adapted for insertion into the intermediate shell, the inner shell having a substantially hemispherical outer surface cooperating with the inner surface of the intermediate shell, the inner shell having at least one attachment element rigidly and non-rotatably coupled to the outer shell with respect to the main axis;

a joint head positioned within the inner shell; and wherein the outer surface of the intermediate shell comprises a supporting portion for bearing against the recessed portion of the inner surface of the outer shell and a non-supporting portion spaced from the inner surface of the outer shell by a predetermined distance to allow movement of the intermediate shell, the inner shell and at least one of the movable segments of the outer shell, transversely to the main axis of the outer shell.

2. The socket of claim 1 wherein the outer surface of the intermediate shell has a first radius and the inner surface of the outer shell has a second radius, the difference between the first and second radii being substantially equal to the predetermined distance between the non-supporting portion of the outer surface of the intermediate shell and the inner surface of the outer shell.

3. The socket of claim 1 wherein the outer surface of the outer shell comprises a plurality of projections for attaching the movable segments to the osseous tissue.

4. The socket of claim 1 wherein the outer shell has a wall thickness which allows elastic deformation of the movable segments.

5. The socket of claim 1 wherein the outer shell has a pole region and an equatorial region, a wall thickness of the pole region being smaller than a wall thickness of the equatorial region.

6. The socket of claim 1 wherein the outer and inner surfaces of the intermediate shell are eccentric to each other.

7. The socket of claim 1 wherein the outer shell comprises a contact portion in the region of the main axis projecting inwardly, the contact portion having a contact surface contacting the inner shell and an inwardly open guiding bore, the intermediate shell having an aperture for receiving the contact portion of the outer shell and a supporting surface for bearing against the contact surface of the contact portion, the intermediate shell further comprising a pin-shaped guiding portion projecting outwardly from the supporting surface into the guiding bore of the contact portion.

8. The socket of claim 7 wherein the attachment element comprises a center pin arranged eccentrically relative to the main axis, the guiding bore of the outer shell having a recess for receiving the center pin.

9. The socket of claim 1 wherein the main axis of the outer and inner shells is substantially coincident with a line of action of a main loading force transmitted through the socket.

10. A hip joint prosthesis comprising a composite artificial socket, the socket comprising:

an outer shell having a substantially hemispherical inner surface with a main axis extending in a substantially radial direction, the outer shell being adapted for insertion into an implantation zone, the outer shell having recesses extending along meridians in the outer shell, the recesses defining movable segments adapted for attachment to osseous tissue within the implantation zone;

an intermediate shell having substantially hemispherical inner and outer surfaces;

an inner shell adapted for insertion into the intermediate shell, the inner shell having a substantially hemispherical outer surface cooperating with the inner surface of the intermediate shell, the inner shell having at least one attachment element rigidly and non-rotatably coupled to the outer shell with respect to the main axis;

a joint head positioned within the inner shell; and wherein the outer surface of the intermediate shell comprises a supporting portion for bearing against the recessed portion of the inner surface of the outer shell and a non-supporting portion spaced from the inner surface of the outer shell by a predetermined distance to allow movement of the intermediate shell, the inner shell and at least one of the movable segments of the outer shell, transversely to the main axis of the outer shell.

* * * * *